US007337946B2

(12) United States Patent
Belton

(10) Patent No.: US 7,337,946 B2
(45) Date of Patent: Mar. 4, 2008

(54) DEVICE FOR RESOLVING INTERPERSONAL RELATIONSHIP ISSUES

(75) Inventor: Timothy Belton, Sheridan, WY (US)

(73) Assignee: AnsweRing, LLC, Sheridan, WY (US)

( * ) Notice: Subject to any disclaimer, the term of this patent is extended or adjusted under 35 U.S.C. 154(b) by 234 days.

(21) Appl. No.: 11/263,272

(22) Filed: Oct. 31, 2005

(65) Prior Publication Data

US 2007/0095886 A1 May 3, 2007

(51) Int. Cl.
*G06C 3/00* (2006.01)
*G06C 1/00* (2006.01)
*G06C 27/00* (2006.01)
*G06G 1/14* (2006.01)
*G01G 19/41* (2006.01)
*A61B 5/22* (2006.01)
*G01P 11/00* (2006.01)

(52) U.S. Cl. .............. 235/89 R; 235/89 A; 235/85 FC; 235/61 R; 235/78 R

(58) Field of Classification Search .............. 235/61 R, 235/89 R, 78 R, 78 RC, 88 R, 116, 120, 235/85 FC, 89 A; 402/73, 78, 79
See application file for complete search history.

(56) References Cited

U.S. PATENT DOCUMENTS

| | | | | | |
|---|---|---|---|---|---|
| 1,056,775 | A | * | 3/1913 | Brunton | 235/84 |
| 1,266,142 | A | * | 5/1918 | Motsch | 40/342 |
| 1,312,797 | A | | 8/1919 | Mayer | |
| 1,966,971 | A | * | 7/1934 | Rochlus | 40/495 |
| D138,224 | S | | 7/1944 | Golub et al. | |
| 2,614,751 | A | * | 10/1952 | Heinz, Sr. | 235/89 R |
| 3,100,601 | A | * | 8/1963 | Shapiro | 235/61 B |
| 3,215,344 | A | * | 11/1965 | Joffe | 235/78 RC |
| 3,253,780 | A | * | 5/1966 | Stewart et al. | 235/78 A |
| 3,275,235 | A | * | 9/1966 | Balch | 235/84 |
| 3,309,017 | A | * | 3/1967 | Koskela | 235/78 R |
| 3,572,584 | A | * | 3/1971 | Weaver et al. | 235/88 R |
| 3,598,308 | A | * | 8/1971 | Garcia, Jr. | 235/88 R |
| 3,609,299 | A | * | 9/1971 | Wright | 235/61 NV |
| 3,627,200 | A | * | 12/1971 | Sadler | 235/88 G |
| 3,630,435 | A | * | 12/1971 | Titus | 235/78 R |
| 3,640,453 | A | * | 2/1972 | Caillouet | 235/78 R |
| 3,643,859 | A | * | 2/1972 | Kreisel, Jr. | 235/88 F |
| 3,654,436 | A | * | 4/1972 | Sansom, Jr. | 235/78 R |
| 3,677,467 | A | * | 7/1972 | Pierce | 235/78 R |
| 3,693,872 | A | * | 9/1972 | Titus | 235/78 N |
| 3,698,630 | A | * | 10/1972 | Dick et al. | 235/78 R |
| 3,716,237 | A | * | 2/1973 | Locher | 273/142 H |
| 3,720,369 | A | * | 3/1973 | Alvarado | 235/78 R |
| 3,747,845 | A | * | 7/1973 | Portuesi | 235/78 R |
| 3,747,846 | A | * | 7/1973 | Long | 235/84 |

(Continued)

*Primary Examiner*—Daniel Walsh
(74) *Attorney, Agent, or Firm*—Antoinette M. Tease

(57) ABSTRACT

A device for resolving interpersonal relationship issues comprising: (a) a plurality of text sheets comprised of flexible, transparent material; (b) a rigid front cover; and (c) a rigid back cover; wherein each text sheet comprises an opaque band bearing text on either side of the opaque band, such that different text is presented on each side of the text sheet; wherein both the front and back covers comprise one or more text windows through which the text on the opaque band of the text sheets can be viewed. The text that is presented on one side of each disc relates to one or more interpersonal problem(s) and the text that is presented on the other side of each disc relates to possible solutions to the problem(s). In a preferred embodiment, the text sheets are comprised of MYLAR® polyester film.

13 Claims, 7 Drawing Sheets

U.S. PATENT DOCUMENTS

| | | | | | |
|---|---|---|---|---|---|
| 3,757,092 | A | * | 9/1973 | Miller | 235/74 |
| 3,803,389 | A | * | 4/1974 | Yelverton | 235/78 N |
| 3,858,798 | A | * | 1/1975 | Feingold | 235/83 |
| 3,986,002 | A | * | 10/1976 | DeMaio | 235/78 R |
| 4,149,068 | A | * | 4/1979 | Simon | 235/78 R |
| 4,221,326 | A | | 9/1980 | Kandpal | |
| 4,248,458 | A | | 2/1981 | Brody | |
| 4,317,404 | A | * | 3/1982 | Lombardo | 84/474 |
| 4,323,609 | A | * | 4/1982 | Bromberg | 428/66.6 |
| 4,568,822 | A | * | 2/1986 | Betzko | 235/78 R |
| 4,573,821 | A | * | 3/1986 | Gilreath | 402/78 |
| 4,633,070 | A | * | 12/1986 | Merkh | 235/88 M |
| D289,905 | S | * | 5/1987 | Goldring | D19/25 |
| 4,752,674 | A | * | 6/1988 | Rosenwaks | 235/88 RC |
| 4,819,962 | A | * | 4/1989 | Takai | 281/15.1 |
| 4,882,472 | A | * | 11/1989 | Sigman et al. | 235/88 R |
| 4,918,412 | A | * | 4/1990 | Churchill | 235/88 R |
| 5,054,817 | A | * | 10/1991 | Geinert | 283/66.1 |
| 5,249,827 | A | * | 10/1993 | Olson | 283/36 |
| 5,481,093 | A | * | 1/1996 | Rogerson | 235/78 R |
| 6,265,651 | B1 | * | 7/2001 | Landtroop | 84/471 R |
| 6,460,762 | B1 | | 10/2002 | Bromberg et al. | |
| 6,488,202 | B1 | * | 12/2002 | Seitz et al. | 235/78 R |
| 6,511,246 | B2 | * | 1/2003 | Sapienza et al. | 402/79 |
| 6,569,040 | B2 | * | 5/2003 | Bradstock | 473/407 |
| 6,758,498 | B2 | * | 7/2004 | Sapienza et al. | 283/36 |
| 6,776,437 | B1 | * | 8/2004 | Ho | 283/38 |
| 6,886,740 | B1 | * | 5/2005 | Craig | 235/85 FC |
| 6,974,274 | B2 | * | 12/2005 | Sapienza et al. | 402/79 |
| 6,983,887 | B2 | * | 1/2006 | Holland | 235/475 |
| 2002/0033595 | A1 | * | 3/2002 | Sapienza et al. | 283/37 |
| 2002/0094226 | A1 | * | 7/2002 | Sapienza et al. | 402/79 |
| 2003/0024974 | A1 | * | 2/2003 | Bromberg | 235/78 R |
| 2004/0169070 | A1 | * | 9/2004 | Bromberg et al. | 235/78 R |
| 2004/0251301 | A1 | * | 12/2004 | Niemann et al. | 235/77 |
| 2006/0029909 | A1 | * | 2/2006 | Kaczkowski | 434/98 |
| 2007/0095886 | A1 | * | 5/2007 | Belton | 235/89 R |

* cited by examiner

DEVICE FOR RESOLVING INTERPERSONAL RELATIONSHIP ISSUES

BACKGROUND OF THE INVENTION

1. Field of the Invention

The present invention relates generally to the field of slide chart-type devices, and more particularly, to a circular slide chart that is designed to provide assistance to the user in resolving interpersonal relationship issues.

2. Description of the Related Art

A number of circular slide chart-type devices have been patented for performing mathematical calculations or providing various types of information. None of these devices, however, possesses the unique configuration of the present invention, nor are they designed to convey information concerning interpersonal relationships. These devices are discussed below.

U.S. Pat. No. 1,312,797 (Mayer, 1919) describes a circular calculator comprising a front plate and two moveable discs, wherein the front plate has a window, through which a number from the first disc is visible. Each of the two discs has on its face a series of numbers arranged circumferentially. The first disc (which lies directly beneath the front plate) has an operating handle or tab and a small notch or window through which a number (from the second or bottom disc) can be viewed. The angular movement of the first disc is limited by two stops. The device has a washer that serves as a bearing around which the discs rotate. Surrounding this washer is a spacing washer, the purpose of which is to prevent frictional contact between the two moveable discs and to allow one disc to be rotated independently of the other. The purpose of this device is to perform mathematical calculations.

U.S. Pat. No. 1,966,971 (Rochlus, 1933) discloses a model selector and style indicator. The device is intended to be used in connection with men's tailoring, and it is comprised of a base, two rotating discs or dials (one carrying data on waist measurements and style group classifications and the other carrying data on chest measurements), and a top cover. The waist dial has a handle and sits directly on top of the base. The chest dial also has a handle and is situated between the waist dial and the top cover. The top cover has three sight windows through which the waist measurement, chest measurement and style group classification can be viewed. The chest dial, which sits on top of the waist dial, has a plurality of particularly arranged openings that allow the data from the waist dial to be visible through the sight windows on the top cover.

U.S. Pat. No. D138,224 (Golub et al., 1943) is a design patent that covers a tax calculator that appears to be comprised of four rotating discs and a central base, with two rotating discs on either side of the base. Each of the four discs has windows through which data from the underlying disc or base can be viewed.

U.S. Pat. No. 3,253,780 (Stewart et al., 1965) provides a calculator for displaying the inter-relationship of a plurality of periodically varying factors when taken from a selected point of reference. In particular, this device was intended to be used to provide data on the inter-relationship between three biorhythm cycles, namely, a 23-day cycle that affects physical strength and endurance, a 28-day cycle that impacts feelings and creativity, and a 33-day cycle that relates to mental acuity. Presumably, if the high points of all three cycles coincide, the user of the device would conclude that his or her mental and physical alertness are at their peak; conversely, if the low points of these cycles coincide, the individual would conclude that strenuous activity should be avoided or extra alertness exercised. The device comprises an opaque base member, two transparent or translucent overlay discs, each of which has a radially extending tab and central hole, and a fan-shaped cursor made of an opaque material. The cursor comprises a window and transparent material overlying the window.

U.S. Pat. No. 3,803,389 (Yelverton, 1974) describes a mechanical calculator designed to assist pilots in conducting area navigation computations. The device comprises a front plate with two windows, two rotatable discs (a course plate and an azimuth plate), a base plate, a third rotatable disc (distance plat) on the reverse side of the base plate, an interchangeable course card, and a removable back plate. The front plate, base plate, course card and back plate each has one or two windows so that the values of the underlying discs or plate (on either side of the base plate) are visible through such windows. On one side of the base plate, the course plate (which lies on top of the azimuth plate) is smaller in diameter than the azimuth plate, which allows the azimuth plate values to be visible through the front plate window. On the reverse side of the base plate, the back plate is smaller in diameter than the course card, which in turn is smaller in diameter than the distance plate. The relative sizes of the discs allow values from the distance plate and course card to be visible through the back plate.

U.S. Pat. No. 4,149,068 (Simon, 1979) discloses an improvement to a circular slide rule. The improvement comprises a plurality of separating spacer elements positioned between the rotatable discs. The purpose of the separating spacer elements is to allow one rotatable disc to be moved independent of the other discs. The spacer elements are not rotatable and are secured either by protruding arms that are joined together and locked to the base of the device or by at least one protuberance that extends from the hole in the center of the spacer element and that mates with a slot in the central hub.

U.S. Pat. No. 4,221,326 (Kandpal, 1980) covers a circular disc calculator for use in computing product investment returns. The device comprises six concentrically arranged rotatable discs. Four of the six discs have one or more windows so that information from the immediately underlying disc is visible through the overlying disc.

U.S. Pat. No. 4,248,458 (Brody, 1981) provides a device for selecting race horse winners. The device comprises three rotatable discs, each one smaller in diameter than the underling disc, a backing plate, and a front cover with apertures. Each of the three movable discs comprises a positioning arm, which is preferably comprised of a transparent plastic material so as not to conceal information on the underlying disc. The discs are preferably formed of a thin, flexible paper, plastic or similar material.

U.S. Pat. No. 4,568,822 (Betzko, 1986) describes a device for determining source, maintenance and recoverability (SMR) codes for component items in a parts inventory for military equipment. The device comprises a central plate with a rotatable disc on either side. Each disc has two apertures through which information on the central plate can be viewed.

U.S. Pat. No. 4,633,070 (Merkh, 1986) discloses a device for converting binary numerals to decimal numerals. The device comprises a top piece, a bottom piece, a plurality of concentrically sized rotatable discs, and a plurality of rectangular-shaped, low-friction, transparent plastic sheets. The transparent plastic sheets separate the rotatable discs from each other and allow each disc to move independently of the others. The top and bottom pieces and plastic sheets are indented to allow the concentric peripheries of the disc to be viewed by the user. Each disc, as well as the top piece, comprises apertures that allow information from the underlying disc to be viewed.

U.S. Pat. No. 6,265,651 (Landtroop, 2001) covers a device for selecting musical instrument strings. The device comprises a plurality of concentrically sized discs, each of which has one or more aperture(s) through which information from the immediately underlying disc can be viewed.

U.S. Pat. No. 6,460,762 (Bromberg et al., 2002) and U.S. Patent Application Pub. No. 2003/0024974 (Bromberg et al.) provide a wheel calculator comprising at least one rigid, compact disc that carries reproducible information on one side and legible information on the other. The device further comprises a transparent rigid disc that also bears legible information and that can be used to perform calculations by moving the transparent disc in relation to the compact disc. If desired, the device can be pulled apart to allow the compact disc to be played. In an alternate embodiment, the compact disc is inserted into a pocket, envelope or plastic blister attached to cardboard backing, and the legible information on the disc is read through indentations or apertures in the pocket, envelope or blister.

U.S. Pat. No. 6,569,040 (Bradstock, 2003) describes a golf club selection calculator comprising three overlying discs, each of which bears a radial legend. The top and center discs each has one or more transparent sections to allow viewing of the information on the underlying disc.

U.S. Pat. No. 6,886,740 (Craig, 2005) discloses an apparatus for calculating time periods relating to fertility. The apparatus comprises a base circular calendar and one or more discs containing information about menstrual cycles and ovulation events. Each overlying disc is smaller in diameter than the immediately underlying disc, which allows information from the underlying discs to be read through an indented top cover. The apparatus further comprises a transparent indicator arm extending from the center of the calculator. The indictor arm is used in conjunction with the information provided on the discs to predict the possibility of pregnancy. Preferably, at least one of the discs is substantially transparent.

U.S. Patent Application Pub. No. 2004/0251301 (Niemann et al.) covers another menstrual cycle calculation device. This device comprises two discs that rotate with respect to each other. One disc provides calendar information, and the other disc provides information concerning a first and second date indicators and at least one range indicator. In one embodiment, one disc is larger in diameter than the other, and information on the periphery of the larger disc is aligned with information on the periphery of the smaller disc. In another embodiment, one of the discs is transparent, and information on the opaque disc is read through the transparent disc. In yet another embodiment, one of the discs contains one or more transparent windows, and information on the other disc is read through the disc with windows.

The present invention is distinct from the inventions discussed above both in terms of structure and purpose. Wheeled chart calculators or display devices have heretofore been used to compare numerical, pictorial, or graphic information. But to the best of the inventor's knowledge, none of these devices has been used for the purpose of providing advice of an interpersonal nature, as is the case with the present invention. Furthermore, whereas wheeled calculators have traditionally relied primarily on window openings in opaque materials to show and compare data, the present invention, while using window openings, uniquely employs two-sided information printed on an opaque band on multiple transparent disks made of flexible and transparent material sandwiched between a rigid front and back cover.

Accordingly, it is an object of the present invention to provide advice on interpersonal relationships in a highly accessible, game-like format that causes the user of the device to open up communications with the person that is the object of concern. It is a further object of the present invention to condense a sufficient amount of common interpersonal problems and their suggested solutions into a device small enough and attractive enough to be of interest to the mass market. The present invention provides more than 117,000 possible problem sets, with a corresponding number of answers.

BRIEF SUMMARY OF THE INVENTION

The present invention is a device for resolving interpersonal relationship issues comprising: (a) a plurality of text sheets comprised of flexible, transparent material; (b) a rigid front cover; and (c) a rigid back cover; wherein each text sheet comprises an opaque band bearing text on either side of the opaque band, such that different text is presented on each side of the text sheet; wherein both the front and back covers comprise one or more text windows through which the text on the opaque band of the text sheets can be viewed. The text that is presented on one side of each disc relates to one or more interpersonal problem(s) and the text that is presented on the other side of each disc relates to possible solutions to the problem(s). In a preferred embodiment, the text sheets are comprised of MYLAR® polyester film.

In one embodiment, the opaque band on each text sheet comprises a plurality of text blocks, wherein each text sheet comprises a perimeter, and wherein the text blocks on any given text sheet are equidistant from the perimeter of the text sheet. Preferably, the opaque bands on each of the text sheets are at different distances from the central hub so that no two opaque bands overlap when the device is assembled. The number of text windows on the front cover preferably equals the number of text sheets, and the number of text windows on the front cover preferably equals the number of text windows on the back cover.

The present invention further comprises: (a) a central hub; and (b) a plurality of slip sheets; wherein the central hub comprises one or more notches; wherein each slip sheet comprises a circular aperture in the center of the slip sheet and one or more tongues extending into the circular aperture; wherein the number of notches on the central hub equals the number of tongues on each slip sheet; wherein the tongues on the slip sheets are inserted into the notches on the central hub so that the slip sheets are kept stationary when the text sheets are rotated; and wherein the central hub is situated between the front and back covers. The slip sheets comprise one or more text windows through which the text on the text sheets can be viewed, and the number of text windows on each slip sheet preferably equals the number of text sheets.

The slip sheets are preferably situated between the text sheets so that each text sheet is directly adjacent to at least one slip sheet and each slip sheet is directly adjacent to at least one text sheet. Each of the text sheets comprises a circular aperture in the center of the text sheet, and wherein the circular aperture lies around the central hub, thereby allowing the text sheets to rotate. Each of the text sheets preferably comprises a tab that facilitates the rotation of the text sheet around the central hub. In one embodiment, the diameter of each text sheet is roughly equal to the diameter of the front cover, and the diameter of the back cover is greater than the diameter of the front cover by an amount that is at least equal to the length of the tabs on the text sheets.

REFERENCE NUMBERS

Figure 1:
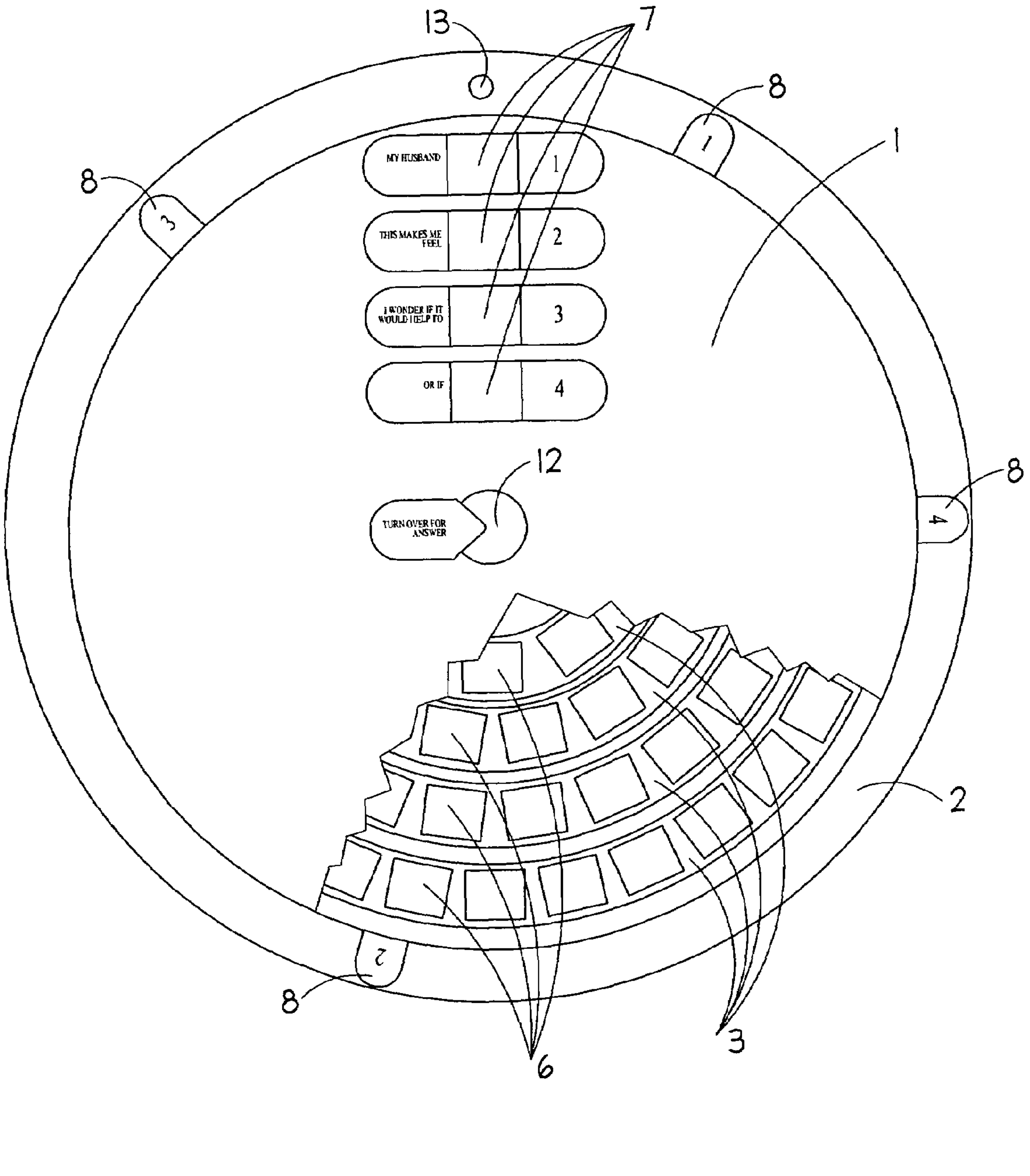
FIG. 1 is a front view of the present invention with a portion of the front cover removed.

1 Front cover
2 Back cover
3 Text sheet
4 Slip sheet
**4*a*** Protection sheet
5 Central hub
6 Text block
7 Text window
8 Tab (on text sheet)
9 Notch (in central hub)
10 Tongue (on slip sheet)
11 Circular aperture (in text and slip sheets and optional protection sheet)
12 Cutout (in central hub and front and back covers)
13 Hole (on back cover, for hanging)

DETAILED DESCRIPTION OF INVENTION

The present invention is a device for resolving interpersonal relationships. The device can be used for wives dealing with husbands, husbands dealing with wives, parents dealing with children, children dealing with parents, employees dealing with bosses, and innumerable other types of interpersonal relationships. The example provided in FIGS. 1 and 2 relates to wives dealing with husbands, but the present invention is not limited to any particular type of interpersonal relationship.

The present invention comprises a front cover 1, a back cover 2, a plurality of text sheets 3, a plurality of slip sheets 4, and a central hub 5. The front cover 1 and text sheets 3 are shown in FIG. 1. Each text sheet 3 comprises a plurality of text blocks 6. The front cover 1 comprises a plurality of text windows 7. Each text sheet 3 comprises a tab 8 that can be utilized to rotate the text sheet 3 so that a particular text block 6 appears in the text window 7. (Please note that the tab 8 on the first text sheet and the corresponding text window 7 on the front cover are labeled as number "4" in the final product. The tab on the second text sheet and the corresponding text window on the front cover are labeled as number "3" in the final product, etc. These numbers are not to be confused with the reference numbers.) In the preferred embodiment, the number of text windows 7 equals the number of text sheets 3, and the text windows 7 are vertically aligned. In the illustration provided in the figures, there are four text sheets 3 and four text windows 7 on the front cover 1. The number of text blocks 6 on any given text sheet 3 will vary depending on the circumference of the text sheet 3 and the size of the text blocks 6. The present invention is not limited to any particular number of text sheets, text windows, or text blocks.

The front cover 1 is preferably comprised of cardboard, injection-molded plastic, or similar rigid material. The text sheets 3 are preferably comprised of a clear plastic sheet material, such as MYLAR® polyester film. The slip sheets 4 do not necessarily need to be transparent; they may be made of any flexible, durable and thin material. The slip sheets 4 allow each text sheet 3 to be rotated without moving any of the other text sheets 3. Because the slip sheets also have text windows 7, and because the text windows 7 on the slip sheets 4 are aligned with the text windows 7 on the front 1 and back 2 covers, text from the underlying text sheets 3 is visible through the text windows 7 on the front 1 or back 2 covers 1, even though there is a slip sheet 4 between each adjacent text sheet 3.

To use the present invention, an individual would use the tabs 8 to rotate each text sheet 3 individually until the desired text appears in each of the text windows 7 on the front cover 1. The example provided in FIG. 1 includes four text windows. The first text window completes the sentence beginning with "My husband . . . " In one embodiment, possible answers include: "has temper tantrums," "is always jealous of other men," "tells me I bore him," and "can't hold down a job." The second text window completes the sentence beginning with "This makes me feel . . . " In one embodiment, possible answers include: "angry," "pretty stupid," "resentful," and "like getting drunk." The third and fourth text windows complete the sentence beginning with "I wonder if it would help to . . . [third text window] or if . . . [fourth text window]." In one embodiment, possible answers include: "confront him with this [or if] it's too late to fix it," "change how I look [or if] it's just my imagination," and "start asserting myself [or if] there's not really a problem."

Figure 2:
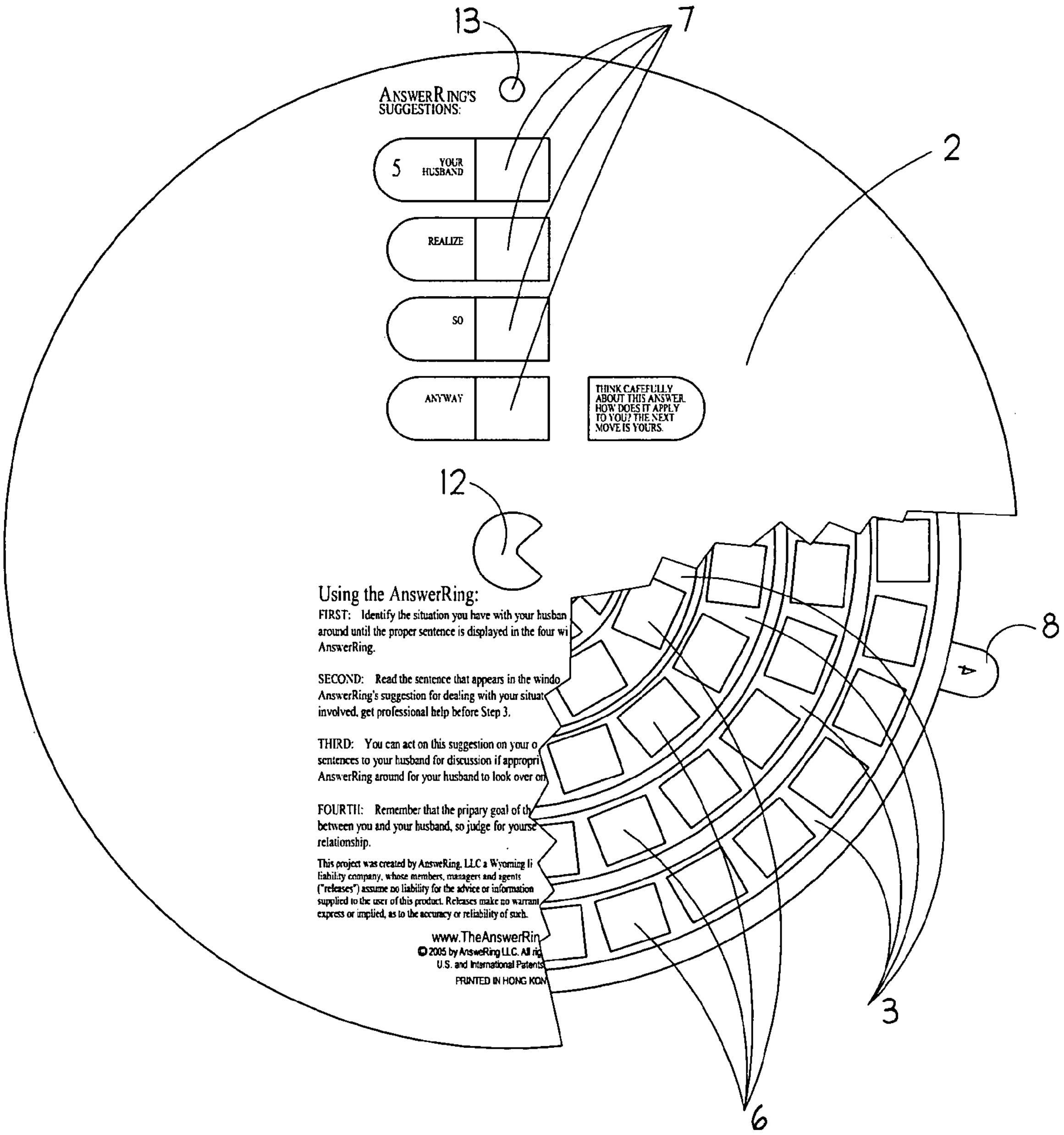
FIG. 2 is a back view of the present invention with a portion of the back cover removed.

Having selected the appropriate text blocks 6 for each of the text windows 7 on the front cover 1, the individual using the present invention would then flip the device over and seek answers on the back cover 2. The back cover 2 and text sheets 3 are shown in FIG. 2. The back cover 2 comprises a plurality of text windows 7, and the number of text windows 7 on the back cover 2 preferably equals the number of text windows 7 on the front cover 1. Furthermore, the text windows 7 on the front 1 and back 2 covers are preferably lined up so that when a text block is aligned with a text window 7 on the front cover 1, it is also aligned with a text window 7 on the back cover 2. The text blocks 6 are printed over a band of opaque ink or paper, which allows a single text block 6 to present different text on either side of the text sheet 3. A single text block 6 will provide a certain text when viewed through the front cover 1 and a different (but specifically related) text when viewed through the back cover 2. Thus, the answers provided on the back cover 2 will be different from but directly related to the information selected on the front cover 1.

Figure 3:
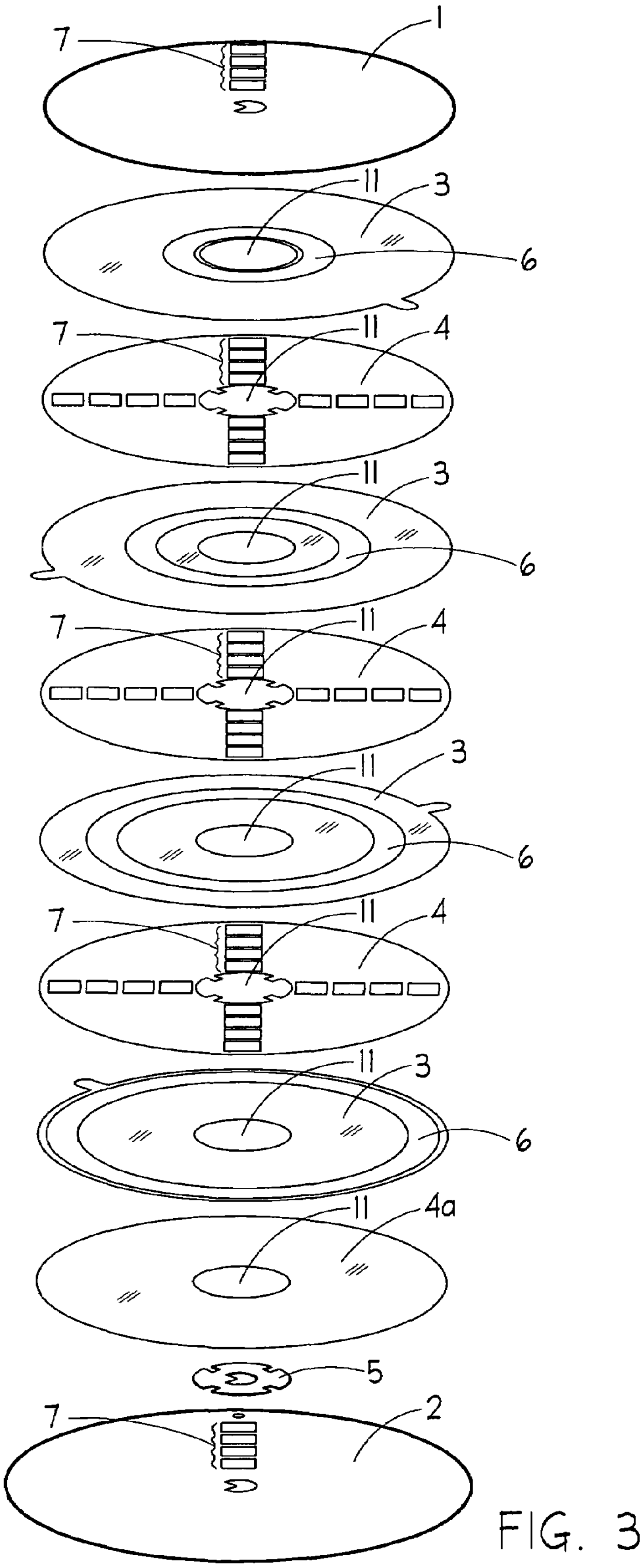
FIG. 3 is an exploded perspective view of the present invention.

FIG. 3 is an exploded perspective view of the present invention. This figure illustrates one potential configuration of the present invention, but the present invention is not limited to any particular number of text sheets 3, slip sheets 4, or text windows 7. As shown in FIG. 3, directly beneath the front cover 1 is a first text sheet 3. Directly beneath the first text sheet 3 is a first slip sheet 4. Directly beneath the first slip sheet 4 is a second text sheet 3. Directly beneath the second text sheet 3 is a second slip sheet 4. Directly beneath the second slip sheet 4 is a third text sheet 3. Directly beneath the third text sheet 3 is a third slip sheet 4. Directly beneath the third slip sheet 4 is a fourth text sheet 3. Directly beneath the fourth text sheet 4 is an optional protection sheet **4*a* (described more fully in connection with FIG. 14**).

The central hub 5 is attached directly to the inside of the front 1 and back 2 covers. The purpose of the central hub 5 is to retain the slip sheets 4 and prevent them from moving. Thus, the central hub 5 comprises a plurality of notches 9 (shown in FIG. 4) into which tongues 10 at the center of the slip sheets 4 (see FIG. 13) extend. These tongues 10 prevent the slip sheets 4 from moving when the text sheets 3 are rotated.

As shown in FIG. 3, each of the text sheets 3 comprises a circular aperture 11 at its center. The diameter of the circular aperture 11 is slightly larger than the diameter of the central hub 5; therefore, each of the text sheets 3 lies around the central hub 5. The slip sheets 4 each has a similar circular aperture 11, except that the circular aperture 11 of the slip sheets 4 comprises a plurality of tongues 10 (shown in greater detail in FIG. 13).

Each of the slip sheets 4 preferably comprises the same number and alignment of text windows 7 as on the front 1 and back 2 covers; however, if the slip sheets 4 were transparent, they could be manufactured without any text windows 7 at all. Even if the slip sheets 4 are transparent, the presence of text windows 7 on the slip sheets 4 reduces the number of clear plastic layers through which the text blocks 6 on the text sheets 3 must be read and, therefore, improves legibility. Technically, each slip sheet 4 need only have one column of text windows 7; however, in the figures, each slip sheet 4 is shown with four columns of text windows 7. Preferably, the slip sheets 4 are manufactured with four columns of text windows 7 to ensure that any positioning of the slip sheets 4 around the central hub 5 will result in proper alignment of the text windows 7.

As shown more clearly in FIGS. 5, 7, 9 and 11, all of the text blocks 6 on a given text sheet 3 are equi-distant from the center of the text sheet 3. In addition, the text blocks 6 on the second text sheet 3 are further from the center of the text sheet than the text blocks on the first text sheet; the text blocks on the third text sheet are further from the center of the text sheet than the text blocks on the second text sheet; and the text blocks on the fourth text sheet are further from the center of the text sheet than the text blocks on the third text sheet. This particular configuration ensures that no text block on any one text sheet obscures the text on another text sheet, and it also allows the text from the first text sheet to be viewed through the text window that is closest to the center of the device (the first text window), the text from the second text sheet to be viewed through the text window that is directly above the first text window (the second text window), the text from the third text sheet to be viewed through the text window that is directly above the second text window (the third text window), and the text from the fourth text sheet to be viewed through the text window that is closest to the perimeter of the device.

Figure 4:
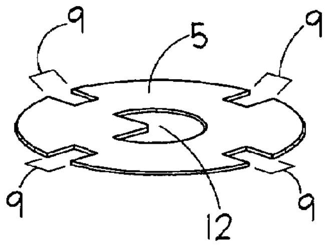
FIG. 4 is a detail perspective view of the central hub of the present invention.

FIG. 4 is a detail perspective view of the central hub 5 of the present invention. As explained above, the central hub comprises a plurality of notches 9 into which the tongues 10 of the slip sheets 4 insert. The central hub 5 optionally comprises a cutout 12, which serves primarily an aesthetic purpose. The central hub is approximately the same thickness as the combined thickness of all the text sheets and slip sheets (and optional protection sheet(s)) combined, in order for it to keep the front 1 and back 2 covers far enough apart to allow the text rings to be easily rotated by the user. The front 1 and back 2 covers optionally comprise a similarly shaped cutout 12.

Figure 5:
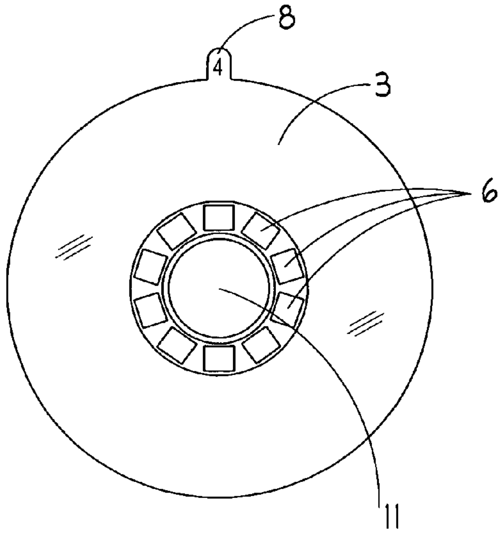
FIG. 5 is a front view of the first text sheet of the present invention.
Figure 6:
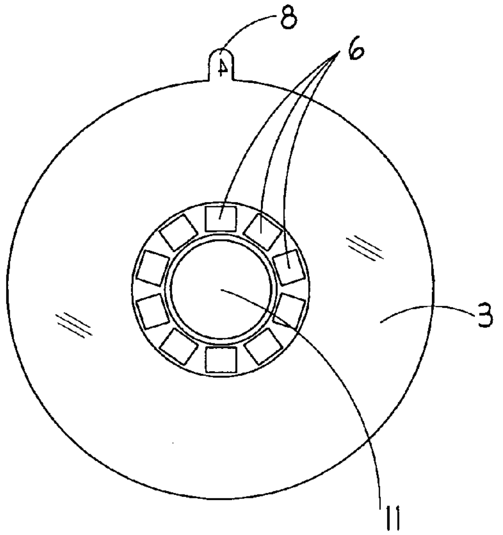
FIG. 6 is a back view of the first text sheet of the present invention.
Figure 7:
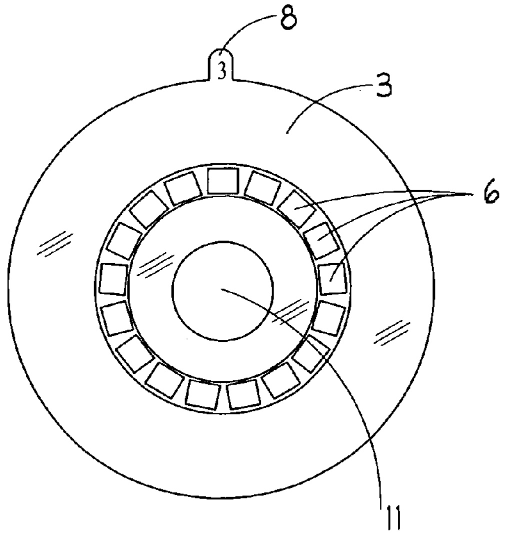
FIG. 7 is a front view of the second text sheet of the present invention.
Figure 8:
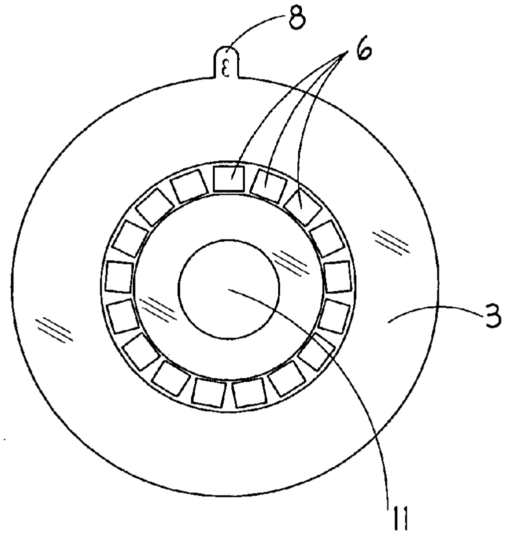
FIG. 8 is a back view of the second text sheet of the present invention.
Figure 9:
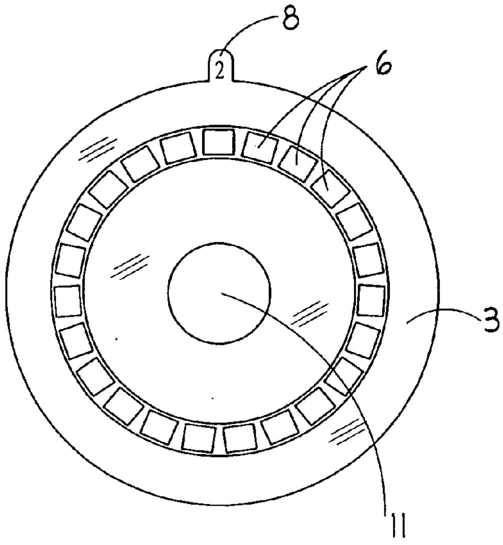
FIG. 9 is a front view of the third text sheet of the present invention.
Figure 10:
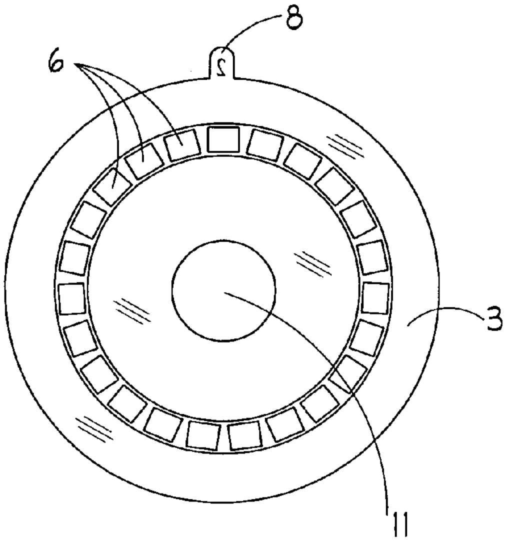
FIG. 10 is a back view of the third text sheet of the present invention.
Figure 11:
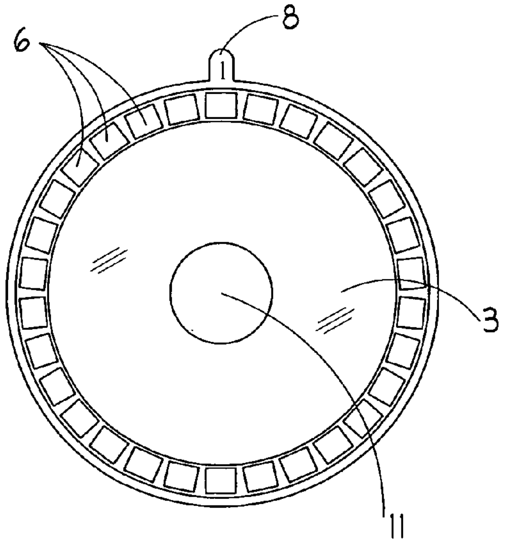
FIG. 11 is a front view of the fourth text sheet of the present invention.
Figure 12:
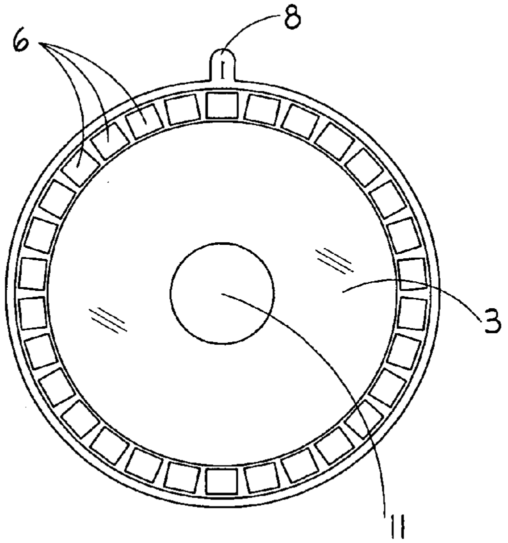
FIG. 12 is a back view of the fourth text sheet of the present invention.

FIG. 5 is a front view and FIG. 6 is a back view of the first text sheet 3 of the present invention. FIG. 7 is a front view and FIG. 8 is a back view of the second text sheet 3 of the present invention. FIG. 9 is a front view and FIG. 10 is a back view of the third text sheet 3 of the present invention. FIG. 11 is a front view and FIG. 12 is a back view of the fourth text sheet 3 of the present invention. As this series of figures illustrates, the text blocks 6 on the first, second, third and fourth text sheets 3 are progressively further from the central hub 5.

Figure 13:
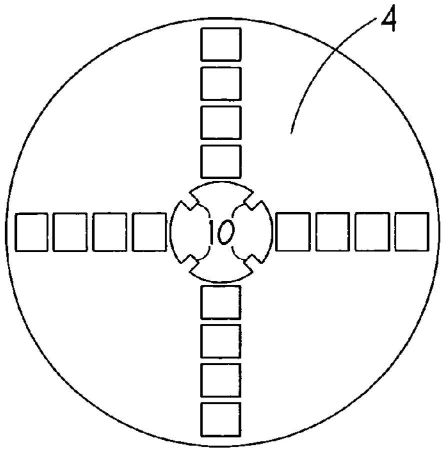
FIG. 13 is a view of either side of the slip sheet of the present invention.

FIG. 13 is a view of either side of the slip sheet 4 of the present invention. The slip sheet 4 comprises a column of vertically aligned text windows 7 and a circular aperture 11 with tongues 10. The number of tongues 10 corresponds to the number of notches 9 in the central hub.

Figure 14:
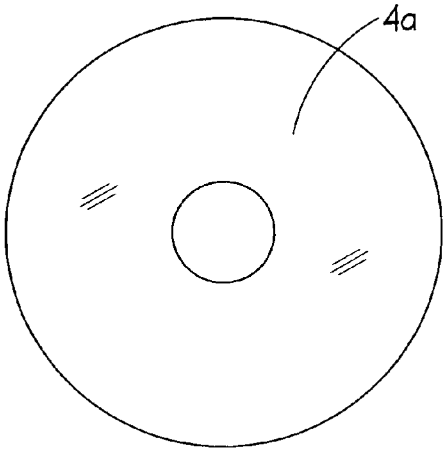
FIG. 14 is a front view of the optional protection sheet of the present invention.
Figure 15:
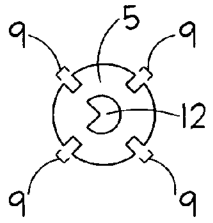
FIG. 15 is a front view of the central hub of the present invention.

FIG. 14 is a front view of the optional protection sheet **4*a* of the present invention. The protection sheet 4*a* is transparent, and it does not have any text windows 7. Preferably, the protection sheet 4*a* is comprised of the same material as the text sheets 3. It does have a circular aperture 11, but the circular aperture 11 does not have any tongues 10. The protection sheet 4*a* may optionally be inserted between the fourth text sheet 3 and the back cover 2. The protection sheet 4*a* is allowed to rotate with the fourth text sheet 3 to prevent ink on the fourth text sheet 3 from rubbing off on the inside of the back cover 2. A protection sheet 4*a* may also be used between the first text sheet 3 and the front cover 1. FIG. 15 is a front view of the central hub 5** of the present invention.

Figure 16:
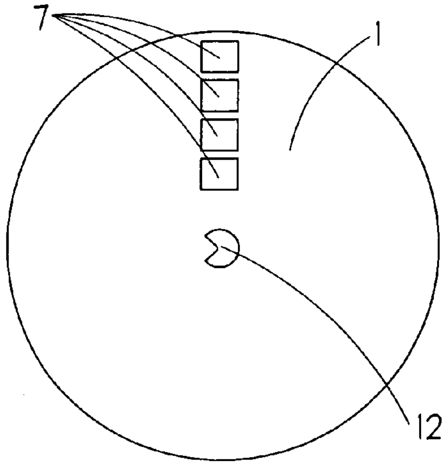
FIG. 16 is a front (outside) view of the front cover of the present invention.
Figure 17:
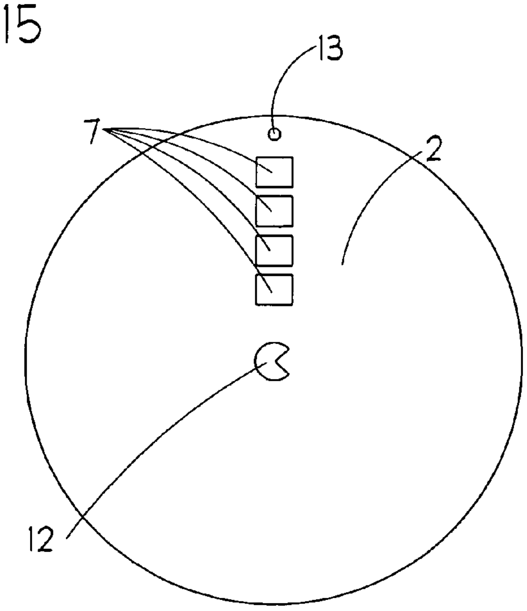
FIG. 17 is a back (outside) view of the back cover of the present invention.

FIG. 16 is a front (outside) view of the front cover 1 of the present invention. FIG. 17 is a back (outside) view of the back cover 2 of the present invention. As is apparent from these two figures, the diameter of the back cover 2 is greater than the diameter of the front cover 1 by an amount that is at least equal to the length of the tabs 8 on the text sheets 3. This difference in diameters between the front 1 and back 2 covers prevents the tabs 8 from being bent or torn because they are supported by the back cover 2. The diameter of the text sheets 3 is roughly equal to the diameter of the front cover 1 (see FIG. 3). The back cover 2 optionally comprises a hole 13 for hanging the device.

Figure 18:
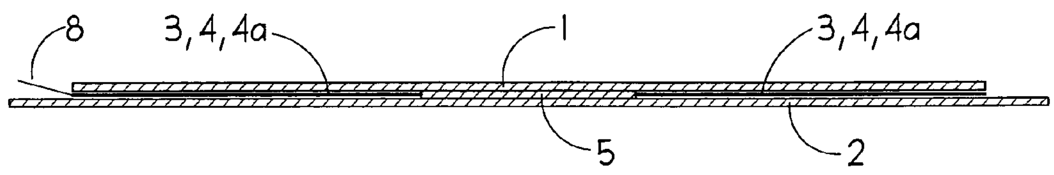
FIG. 18 is a cross-section view of the present invention.
Figure 19:
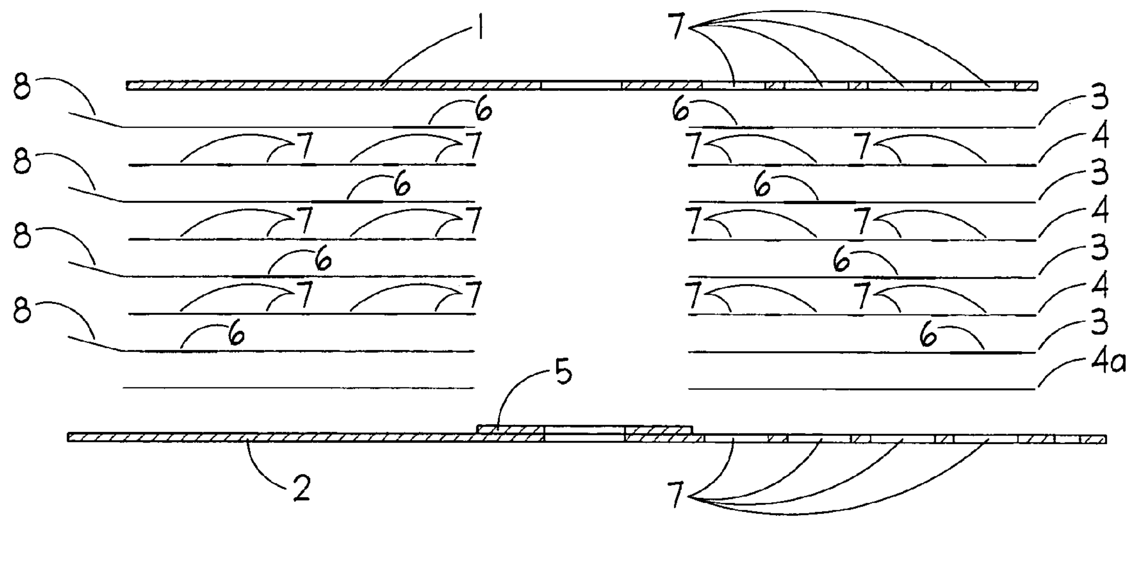
FIG. 19 is an exploded cross-section view of the present invention.

FIG. 18 is a cross-section view of the present invention, and FIG. 19 is an exploded cross-section view of the present invention. When fully compressed, the thickness of the text 3 and slip 4 sheets collectively is no greater than the thickness of the central hub 5. FIG. 19 also illustrates the stair-step configuration of the text blocks 6 on the text sheets 3, a key aspect of the present invention.

Although the preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

I claim:

1. A device for resolving interpersonal relationship issues comprising:

(a) a plurality of text sheets comprised of flexible, transparent material, each text sheet having a top side and a bottom side;

(b) a rigid front cover; and (c) a rigid back cover;

wherein each text sheet comprises an opaque band bearing text thereon on both a top and bottom side of the opaque band, such that different text is presented on each of the top and bottom side of the text sheet;

wherein both the front and back covers comprise one or more text windows through which the text on the opaque bands of each of the text sheets can be viewed.

2. The device of claim 1, wherein the opaque band on each text sheet comprises a plurality of text blocks, wherein each text sheet comprises a perimeter, and wherein the text blocks on any given text sheet are equi-distant from the perimeter of the text sheet.

3. The device of claim 1, wherein the opaque bands on each of the text sheets are at different distances from the central hub so that no two opaque bands overlap when the device is assembled.

4. The device of claim 1, wherein the number of text windows on the front cover equals the number of text sheets, and wherein the number of text windows on the front cover equals the number of text windows on the back cover.

5. The device of claim 1, wherein the text that is presented on one side of each sheet relates to one or more interpersonal problem(s) and the text that is presented on the other side of each sheet relates to possible solutions to the problem(s).

6. The device of claim 1, further comprising:

(a) a central hub; and (b) a plurality of slip sheets;

wherein the central hub comprises one or more notches;

wherein each slip sheet comprises a circular aperture in the center of the slip sheet and one or more tongues extending into the circular aperture;

wherein the number of notches on the central hub equals the number of tongues on each slip sheet;

wherein the tongues on the slip sheets are inserted into the notches on the central hub so that the slip sheets are kept stationary when the text sheets are rotated; and wherein the central hub is situated between the front and back covers.

7. The device of claim 6, wherein the slip sheets are situated between the text sheets so that each text sheet is directly adjacent to at least one slip sheet and each slip sheet is directly adjacent to at least one text sheet.

8. The device of claim 6, wherein each of the text sheets comprises a circular aperture in the center of the text sheet, and wherein the circular aperture lies around the central hub, thereby allowing the text sheets to rotate.

9. The device of claim 8, wherein each of the text sheets further comprises a tab that facilitates the rotation of the text sheet around the central hub.

10. The device of claim 9, wherein the diameter of each text sheet is roughly equal to the diameter of the front cover, and wherein the diameter of the back cover is greater than the diameter of the front cover by an amount that is at least equal to the length of the tabs on the text sheets.

11. The device of claim 6, wherein the slip sheets comprise one or more text windows through which the text on the text sheets can be viewed.

12. The device of claim 11, wherein the number of text windows on each slip sheet equals the number of text sheets.

13. The device of claim 1, wherein the text sheets are comprised of MYLAR® polyester film.

* * * * *